(12) United States Patent
Nett et al.

(10) Patent No.: US 10,335,096 B2
(45) Date of Patent: Jul. 2, 2019

(54) SYSTEM AND METHOD FOR AUXILIARY ANATOMY SCANNING UTILIZING A COMPUTED TOMOGRAPHY (CT) SYSTEM

(71) Applicant: General Electric Company, Schenectady, NY (US)

(72) Inventors: Brian Edward Nett, Wauwatosa, WI (US); Brandon Allan Smith, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 170 days.

(21) Appl. No.: 15/446,611

(22) Filed: Mar. 1, 2017

(65) Prior Publication Data

US 2018/0249970 A1    Sep. 6, 2018

(51) Int. Cl.
*A61B 6/00* (2006.01)
*A61B 6/04* (2006.01)
*H05G 1/00* (2006.01)
*A61B 6/03* (2006.01)
*A61G 1/02* (2006.01)

(52) U.S. Cl.
CPC ............ *A61B 6/032* (2013.01); *A61B 6/0407* (2013.01); *A61B 6/461* (2013.01); *A61B 6/5205* (2013.01); *A61B 6/54* (2013.01); *A61G 1/02* (2013.01); *A61B 6/4435* (2013.01); *A61G 2210/50* (2013.01)

(58) Field of Classification Search
CPC ........... A61B 6/027; A61B 6/032; A61B 6/04; A61B 6/0457; A61B 6/0407; A61B 6/4435; A61B 6/461; A61B 6/5205; A61B 6/54; A61B 6/035; A61B 6/08; A61B 6/463; A61B 6/465; A61B 6/469; A61B 6/481; A61B 6/488; A61B 6/507; A61B 6/5276; A61B 6/542; A61B 6/582; A61B 6/0442; A61B 6/102; A61B 6/4405; A61B 5/0555; A61B 6/10; A61B 2017/00924; A61B 46/10; A61B 6/4417; A61B 6/4423; A61B 6/4441; A61B 6/0421; A61B 6/4447; A61N 2005/1063; A61N 5/1049; G06T 11/006; G06T 2211/421; G06T 11/005; A61G 1/02; A61G 2210/50
USPC ......... 378/209, 208, 20, 68; 5/600, 601, 620
See application file for complete search history.

(56) References Cited

U.S. PATENT DOCUMENTS

| 4,914,682 | A | * | 4/1990 | Blumenthal | ......... A61B 6/0457 378/20 |
| 5,619,763 | A | * | 4/1997 | Randolph | ................ A61B 6/04 378/209 |
| 6,199,233 | B1 | | 3/2001 | Kantrowitz et al. | |
| 6,322,251 | B1 | * | 11/2001 | Ballhaus | ................ A61B 6/035 378/195 |
| 6,857,778 | B2 | | 2/2005 | Mun et al. | |

(Continued)

*Primary Examiner* — Irakli Kiknadze
(74) *Attorney, Agent, or Firm* — Fletcher Yoder, P.C.

(57) ABSTRACT

A method is provided. The method includes partially supporting a subject to be imaged on a board extending from a mobile patient transport into a gantry bore of a stationary computed tomography (CT) imaging system while partially supporting both the subject and the board with a cradle extending from a table. The method also includes acquiring a single imaging volume, during an imaging scan with the stationary CT imaging system, without moving the subject.

13 Claims, 8 Drawing Sheets

(56) References Cited

U.S. PATENT DOCUMENTS

| | | | |
|---|---|---|---|
| 7,293,308 B2* | 11/2007 | Everett | A61B 5/0555 378/20 |
| 8,292,505 B2 | 10/2012 | Tybinkowski et al. | |
| 2004/0055089 A1 | 3/2004 | Dinkler et al. | |
| 2005/0034237 A1* | 2/2005 | Lenting | A61B 5/0555 5/600 |

* cited by examiner

SYSTEM AND METHOD FOR AUXILIARY ANATOMY SCANNING UTILIZING A COMPUTED TOMOGRAPHY (CT) SYSTEM

BACKGROUND

The subject matter disclosed herein relates to medical imaging and, in particular, to techniques for auxiliary anatomy scanning utilizing a computed tomography (CT) imaging system.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the emission of gamma radiation, to acquire data and to construct images or otherwise represent the observed internal features of the patient.

Traditionally, medical imaging systems, such as a computed tomography (CT) imaging system or a CT/positron emission tomography (PET) imaging system, include a gantry and a patient table. Typically, a patient is moved into imaging room and transferred to a patient support on the patient table. Moving the patient onto the patient support can be burdensome (and pose a risk of injury) to the technologists and disruptive to the patient.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with a first embodiment, a method is provided. The method includes partially supporting a subject to be imaged on a board extending from a mobile patient transport into a gantry bore of a stationary computed tomography (CT) imaging system while partially supporting both the subject and the board with a cradle extending from a table. The method also includes acquiring a single imaging volume, during an imaging scan with the stationary CT imaging system, without moving the subject.

In accordance with a second embodiment, a method is provided. The method includes positioning a board both supporting a subject to be imaged and coupled to a mobile patient transport into a gantry bore of a stationary computed tomography (CT) imaging system utilizing a cradle extending from a table. The method also includes acquiring a single imaging volume, during an imaging scan with the stationary CT imaging system, without moving the subject.

In accordance with a third embodiment, a method is provided. The method includes supporting a subject to be imaged on a board extending from a mobile patient transport into a gantry bore of a stationary computed tomography (CT) imaging system. The method also includes acquiring a single imaging volume, during an imaging scan with the stationary CT imaging system, without moving the subject.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
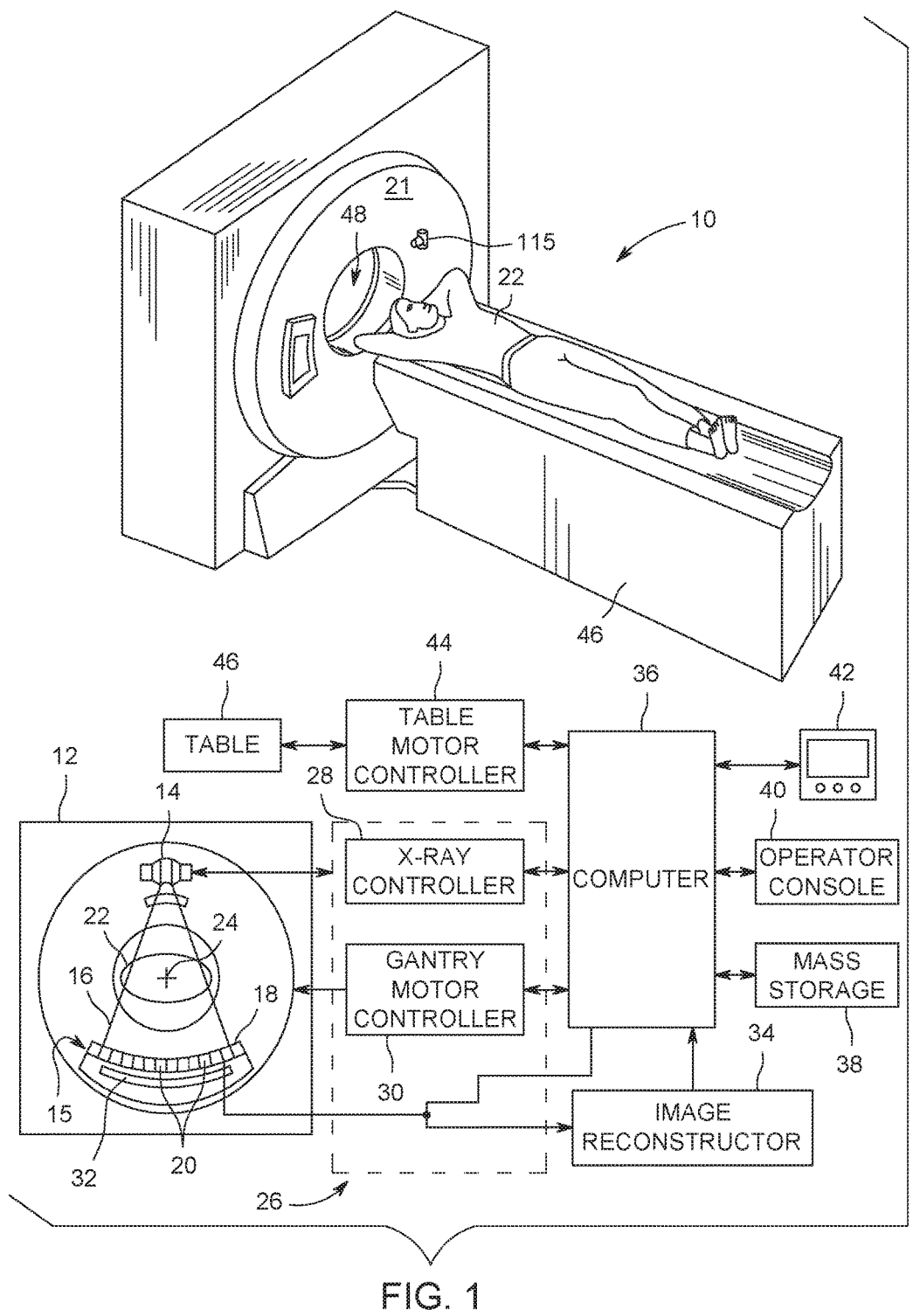
FIG. 1 is a combined pictorial view and block diagram of a computed tomography (CT) imaging system as discussed herein.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The presently contemplated embodiments enable alternative or auxiliary techniques for both preparing a patient for imaging and imaging the patient utilizing a medical imaging system (e.g., computed tomography (CT) or CT/positron emission tomography (PET) imaging system). In particular, a patient (e.g., subject) may be scanned and a single imaging volume (e.g., utilizing 160 millimeter (mm) collimation) acquired without moving the patient during the scan (e.g., mid-scan) while the imaging system is stationary. In certain embodiments, a patient may disposed on a support (e.g., transfer board, extension, etc.) disposed on or coupled to a mobile patient transport (e.g., gurney) separate from the imaging system on a first side of a gantry bore of the imaging system. The patient is then extended (while on the support)

from the gurney into the gantry bore for the scan. In certain embodiments, the support is extended (while supporting the patient) into the gantry bore so that the support and the gurney completely support the patient during the scan. In other embodiments, a patient support (e.g., cradle) coupled to a table may be disposed on the other side of the gantry bore (e.g., opposite from the gurney). The patient support coupled to the table may include an accessory or extension configured to couple (e.g., via a corresponding accessory or receptacle) to the support (while supporting the patient) on the gurney. The patient support while coupled to the support may adjust a position (e.g., pull) of the support so that it and the patient are extended into the gantry bore for the scan. In this embodiment, the patient support would only partially support both the subject and the board, while the support or board coupled to the gurney supports a majority of the patient. In certain embodiments, the support may be thinner than the patient support (e.g., cradle) and, thus, more transmissive to X-rays improving X-ray flux and enabling optimization of X-ray dose. In addition, the disclosed embodiments enable an alternative workflow for scans that do not require repositioning of a patient during a scan or do not require a CT table. Further, the handling of the patient (via technologists) is reduced or avoided in positioning them for the scan.

Although the following embodiments are discussed in terms of a computed tomography (CT) imaging system, the embodiments may also be utilized with other imaging systems (e.g., PET, CT/PET, SPECT, nuclear CT, etc.). With the preceding in mind and referring to FIG. 1, a CT imaging system 10 is shown, by way of example. The CT imaging system includes a gantry 12. The gantry 12 has an X-ray source 14 that projects a beam of X-rays 16 toward a detector assembly 15 on the opposite side of the gantry 12. The detector assembly 15 includes a collimator assembly 18, a plurality of detector modules 20, and data acquisition systems (DAS) 32. The plurality of detector modules 20 detect the projected X-rays that pass through a patient 22, and DAS 32 converts the data to digital signals for subsequent processing. Each detector module 20 in a conventional system produces an analog electrical signal that represents the intensity of an incident X-ray beam and hence the attenuated beam as it passes through the patient 22. During a scan to acquire X-ray projection data, gantry 12 and the components mounted thereon rotate about a center of rotation 24 so as to collect attenuation data from a multitude of view angles relative to the imaged volume.

Rotation of gantry 12 and the operation of X-ray source 14 are governed by a control mechanism 26 of CT system 10. Control mechanism 26 includes an X-ray controller 28 that provides power and timing signals to an X-ray source 14 and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44, which controls a motorized table 46 (and/or patient support such as a cradle) to position patient 22 relative to the gantry 12. Particularly, table 46 moves (e.g., extends) portions of patient 22 on the patient support through a gantry opening or bore 48. As described in greater detail below, the patient support (e.g., cradle) includes an accessory or extension that enables the patient support to move or position (e.g., pull) the patient 22 into gantry bore 48 while the patient 22 is disposed on a support (e.g., board or extension) coupled to a gurney on the opposite side of the gantry 12.

Figure 2:
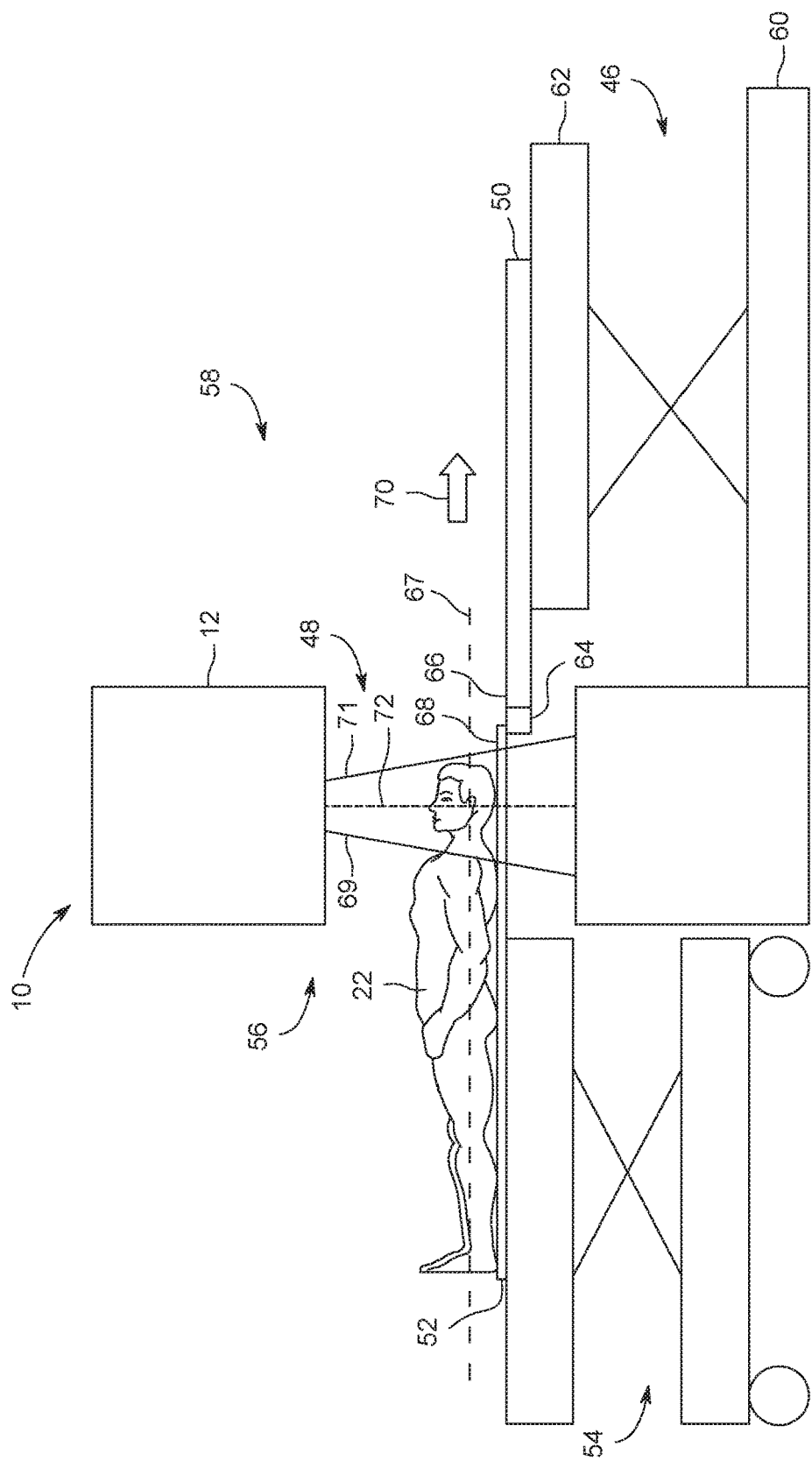
FIG. 2 is a schematic diagram of an embodiment of a patient support being utilized to position a patient within a bore of a gantry.

FIG. 2 is a schematic diagram of an embodiment of a patient support 50 (e.g., cradle) being utilized to position the patient 22 within the bore 48 of the gantry 12. As depicted, the patient 22 is disposed on a support 52 (e.g., extension or transfer board) disposed on or coupled to a mobile patient transport (e.g., gurney 54) on a first side 56 of the gantry 12 (and bore 48). In certain embodiments, the support 52 is merely disposed on (and separate from) the gurney 54. In other embodiments, the support 52 is coupled to and/or part of the gurney 54. The patient 22 is positioned within the room in the extra space behind the gantry 12 (i.e., side 56). As depicted, the patient support 50 is coupled to the table 46. The table 46 and the patient support 50 are disposed on a second side 58 of the gantry 12 (and bore) opposite side 56. The structure of the table 46 may vary. As depicted, the table 46 includes a table base 60 and an upper table 62 coupled to the table base 60. A height of the table 46 (or the upper table 62 relative to the table base 60) may be adjustable (e.g., via controller 44). The patient support 50 is coupled to the table 46 (e.g., upper table 62). The patient support 50 is configured to move (e.g., axially) relative to the table 46 (e.g., via controller 44). As depicted, the support 52 (e.g., made of plastic, carbon fiber, etc.) is thinner than the patient support 50. As a result, the support 52 is more transmissive (e.g., relative to the patient support 50) to X-rays improving X-ray flux and enabling optimization of X-ray dose during an imaging scan.

The patient support 50 includes an accessory or extension 64 coupled to an end 66 of the patient support 50 nearest the gantry 12 (and bore 48). The accessory or extension 64 is configured to couple to an end 68 of the support 52. In certain embodiments, the extension 64 may include a structure (e.g., hook, protrusion, etc.) configured to couple to (e.g., be received by) a corresponding structure (e.g., accessory, receptacle, opening, etc.) on the end 68 of the support 52. In certain embodiments, the patient support 50 may be extended axially (e.g., via controller 44) through the bore 48 towards the support 52 (with the patient 22 on it) on the gurney 54. A height of the patient support 50 may be adjusted (e.g., via controller 44) to enable the extension 64 (e.g., the structure) to couple to the corresponding structure on the end 68 of the support 52. In certain embodiments, a laser) or laser plane 67 may be utilized as a guide by a user to ensure a height of the patient support 50 is properly aligned with respect to a height of the support 52. For example, the laser 67 may represent a height where when the patient 22 is aligned with the laser 67 or a height of the patient support 50 is aligned with a height of the support 52. Additionally, a laser projection system may be utilized to display the physical size of the imaging beam (e.g., collimation as indicated by lasers 69, 71). This would be useful for centering the patient within the scanner. The lasers 69, 71 may also be utilized by the user to adjust the X-ray collimation. In addition, in response to adjustments in X-ray collimation, the laser projection system may adjust the position of the lasers to show the prescribed beam.

Upon coupling of the extension 64 to the support 52, a position of the support 52 is adjusted via the patient support 50. Specifically, the patient support 50 may be moved (e.g., via controller 44) axially in direction 70 to pull the support 52 and patient 22 into the bore 48 so that the portion of the patient to be imaged will be disposed within a scan plane 72 of the gantry 12. With the support 52 and portion of patient 22 to be imaged extending into the bore 48, a majority of the patient 22 (i.e., patient's weight) is being supported by the support 52 and/or the gurney 54. The patient support 50 extending from the table 46 only partially supports (e.g., providing less support than the support 52 and/or the gurney 54) the patient 22 and the support 52. In certain embodiments, a distance the patient support 50 moves in the direction 70 may be limited (e.g., via controller 44) to keep from pulling the patient 22 and the support 52 off of the gurney 54. In certain embodiments, once the patient 22 and the support 52 are extended into position for the scan, a position of the patient support may be locked (e.g., via controller 44) to avoid unintended motion while the patient 22 is being partially supported by the patient support 50.

During the process of moving the support 52 and the patient 22 into the bore 48, the gantry 12 (and CT system 10), gurney 54, and table 46 (with the exception of cradle 50) are kept stationary. The CT system 10 (other than the rotation of the gantry 12 in place) is stationary (e.g., does not move in an axial direction) during the scan. Also, during the scan, a single imaging volume (e.g., utilizing up to 160 mm collimation) may be acquired without moving the patient 22 during the scan (e.g., mid-scan). In order to improve patient throughput on the system 10, multiple gurneys 54 and transfer boards 52 may be purchased by the hospital and patient preparation may be performed in a separate room.

Figure 3:
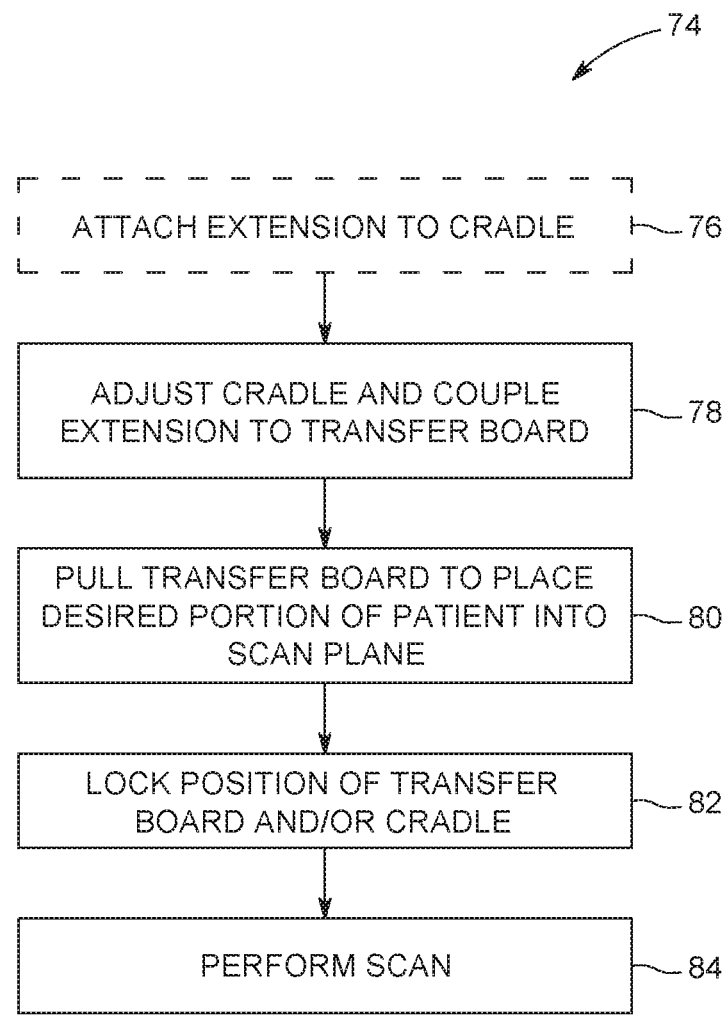
FIG. 3 is a flow chart of an embodiment of a method for positioning a patient for imaging utilizing a patient support.

FIG. 3 is a flow chart of an embodiment of a method 74 for positioning the patient 22 for imaging utilizing the patient support 50. One or more the steps of the method 74 may be carried out utilizing the controllers 28, 30, 44. In certain embodiments, the method 74 includes attaching the extension 64 to the end 66 of the patient support 50 (block 76). In certain embodiments, the extension 64 may be part of the patient support 50. The method 74 includes adjusting a position of the patient support 50 to couple the extension 64 to the end 68 of the support 52 (block 78). For example, the patient support 50 may initially be extended axially (e.g., via controller 44) through the bore 48 towards the support 52 (with the patient 22 on it) on the gurney 54. Also, a height of the patient support 50 may be adjusted (e.g., via controller 44) to enable the extension 64 (e.g., the structure) to couple to the corresponding structure on the end 68 of the support 52. In certain embodiments, a laser) or laser plane 67 may be utilized as a guide by a user to ensure a height of the patient support 50 is properly aligned (e.g., vertically) with respect to a height of the support 52. For example, the laser 67 may represent a height where when the patient 22 is aligned with the laser 67 or a height of the patient support 50 is aligned with a height of the support 52. Additionally, a laser projection system may be utilized to display the physical size of the imaging beam (e.g., collimation as indicated by lasers 69, 71). This would be useful for centering the patient within the scanner. The lasers 69, 71 may also be utilized by the user to adjust the X-ray collimation. In addition, in response to adjustments in X-ray collimation, the laser projection system may adjust the position of the lasers to show the prescribed beam. The method 74 also includes moving (e.g., pulling) the support 52 (and the patient 22) to place the desired portion of the patient 22 to be scanned into the bore 48 and the scan plane 72 (block 80). As noted above, during the process of moving the support 52 and the patient 22 into the bore 48, the gantry 12 (and CT system 10), gurney 54, and table 46 are kept stationary. With the support 52 and portion of patient 22 to be imaged extending into the bore 48, a majority of the patient 22 (i.e., patient's weight) is being supported by the support 52 and/or the gurney 54. The patient support 50 extending from the table 46 only partially supports (e.g., providing less support than the support 52 and/or the gurney 54) the patient 22 and the support 52. Upon getting the patient into position for the scan, the method 74 may include subsequently locking a position of the patient support 50 and/or transfer board 52 to avoid unintended motion while the patient 22 is being partially supported by the patient support 50 (block 82). The method 74 further includes performing the scan (e.g., with a stationary CT imaging system 10) to acquire a single imaging volume without moving the patient during the scan (block 84).

Figure 4:
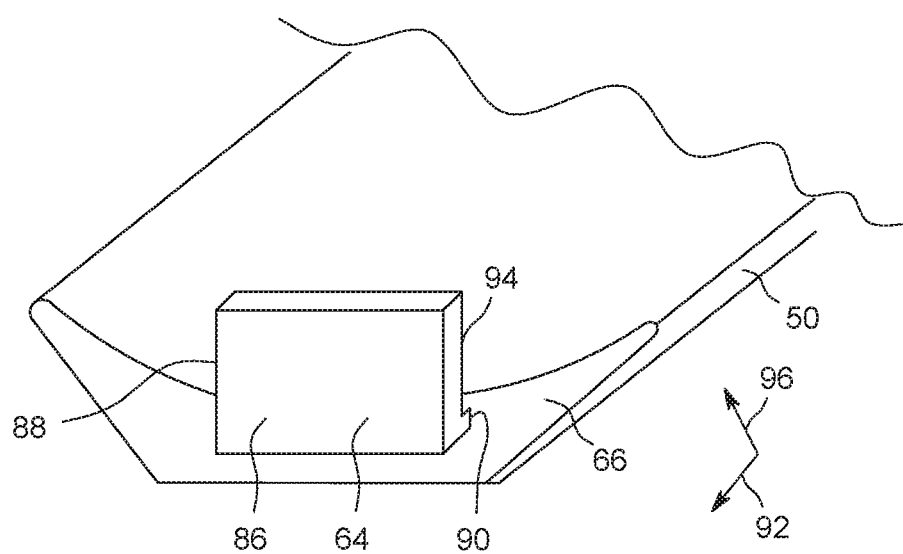
FIG. 4 is a perspective view of an embodiment of an accessory or extension coupled to a patient support.

FIG. 4 is a perspective view of an embodiment of the accessory or extension 64 coupled to the patient support 50 (e.g., cradle). As depicted, the extension 64 is coupled to the end 66 of the patient support 50. The accessory or extension 64 is configured to couple to the end 68 of the support 52. As depicted, the extension 64 includes a structure 86. The structure 86 includes a hook or protrusion 88 configured to couple to a corresponding structure (e.g., accessory, receptacle, opening, etc.) on the end 68 of the support 52. The shape of the structure 86 may vary. As depicted, the structure 86 includes a first portion 90 extending in an axial direction 92 away from the end of the 68 of the patient support 50. A second portion 94 of the structure 86 extends from the first portion 90 in a radial direction 96. In certain embodiments, the second portion 94 may couple (e.g., fit within or extend into) to the corresponding structure on the end 66 of the support 52. In certain embodiments, the extension 64 is attached to the end 66 of the patient support 50. In certain embodiments, the extension 64 may be part of the patient support 50.

Figure 5:
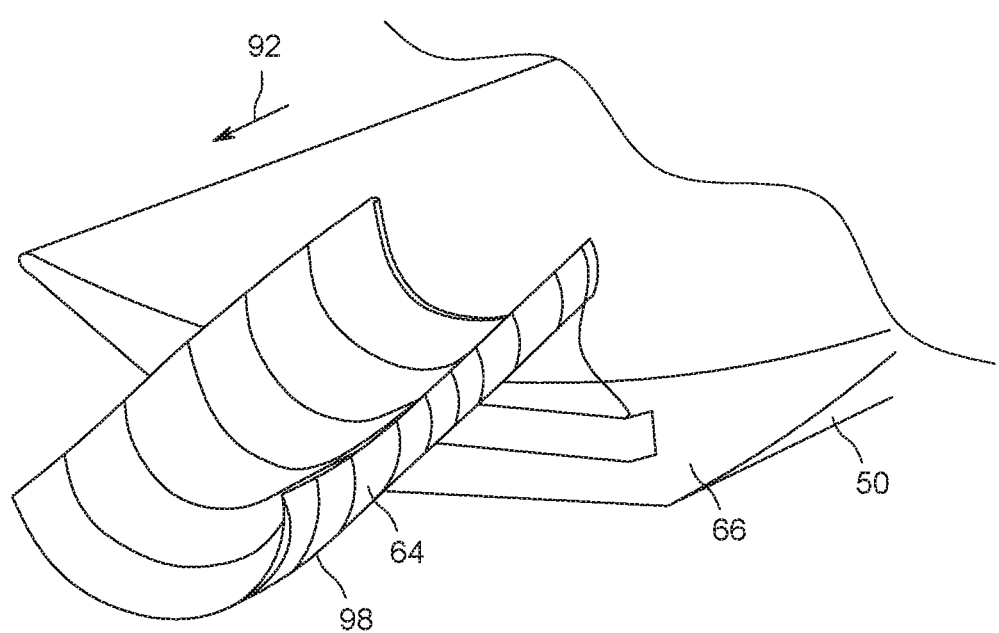
FIG. 5 is a perspective view of an embodiment of an accessory or extension coupled to a patient support (e.g., for supporting an extremity)

FIG. 5 is a perspective view of an embodiment of an accessory or extension 64 coupled to the patient support 50 (e.g., for supporting an extremity). In certain embodiments, the extension 64 may be utilized so that an extremity (hand, arm, foot, leg, etc.) of the patient 22 may be placed on the extension 64 for imaging. For example, the patient support 50 (e.g., cradle) may be extended from the table 46 so that the extension 64 is disposed within the scan plane 72 in the bore 48. The patient 22 is positioned (e.g., via wheelchair) within the room in the extra space behind the gantry 12 (i.e., side 56) and then places the extremity on the extension 64 for the imaging scan. As depicted, the extension 64 is coupled to the end 66 of the patient support 50 (e.g., cradle). In certain embodiments, the extension 64 may be attached to the end 66 of the patient support 50. In other embodiments, the extension 64 may be part of the patient support 50. As depicted, the extension 64 includes a structure 98. The shape of the structure 98 may vary. As depicted, the structure 98 is arcuate-shaped and extends in the axial direction 92 away from the end 66 of the patient support 50. As depicted, the extension 64 (e.g., made of plastic, carbon fiber, etc.) is thinner than the patient support 50. As a result, the support 64 is more transmissive (e.g., relative to the patient support 50) to X-rays improving X-ray flux and enabling optimization of X-ray dose during an imaging scan.

Figure 6:
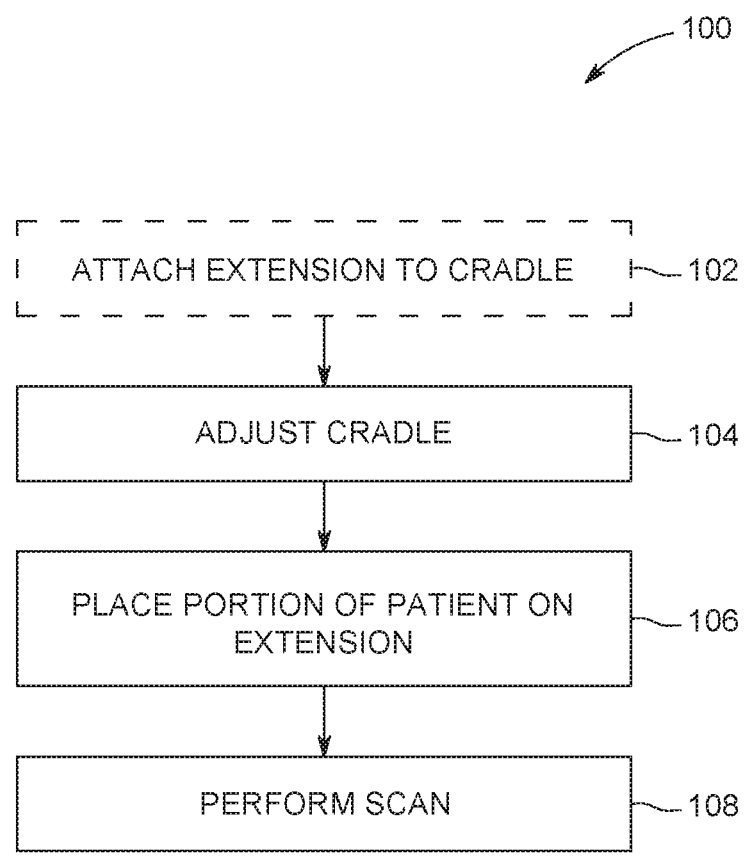
FIG. 6 is a flow chart of an embodiment of a method for imaging an extremity of a patient utilizing an extension coupled to a patient support.

FIG. 6 is a flow chart of an embodiment of a method 100 for imaging an extremity of the patient 22 utilizing the extension 64 (e.g., as depicted in FIG. 5) coupled to the patient support 50. One or more the steps of the method 100 may be carried out utilizing the controllers 28, 30, 44. In certain embodiments, the method 100 includes attaching the extension 64 to the end 66 of the patient support 50 (block 102). In certain embodiments, the extension 64 may be part of the patient support 50. The method 100 includes adjusting a position of the patient support 50 to place the extension 64 within the scan plane 72 in the bore 48 (block 104). For example, the patient support 50 may initially be extended axially (e.g., via controller 44) into the bore 48 towards the patient 22 (e.g., in a wheelchair). Also, a height of the patient support 50 may be adjusted (e.g., via controller 44). The method 102 also placing the desired portion of the patient 22 (e.g., extremity) to be scanned onto the extension 64 in the bore 48 and the scan plane 72 (block 106). As noted above, during the process of moving the support 52 into the bore 48, the gantry 12 (and CT system 10) and table 46 are kept stationary. Upon getting the patient into position for the scan, the method 100 further includes performing the scan (e.g., with a stationary CT imaging system 10) to acquire a single imaging volume without moving the patient during the scan (block 108).

Figure 7:
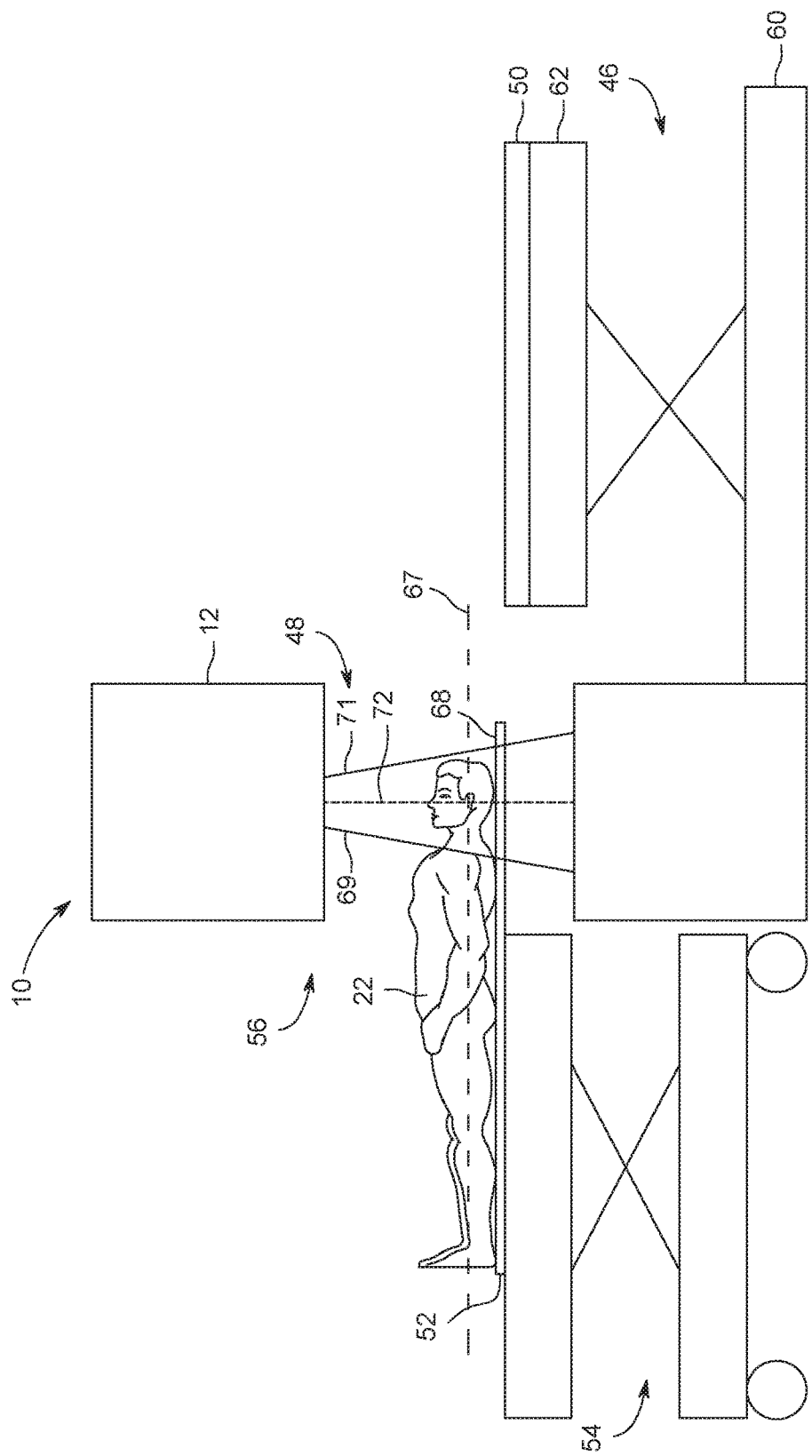
FIG. 7 is a schematic diagram of an embodiment of a patient being supported by a support within a bore of a gantry.

FIG. 7 is a schematic diagram of an embodiment of the patient 22 being supported by the support 52 within the bore 48 of the gantry 12. As depicted, the patient 22 is disposed on the support 52 (e.g., extension or transfer board) disposed on or coupled to the gurney 54 on the first side 56 of the gantry 12 (and bore 48). In certain embodiments, the support 52 is merely disposed on (and separate from) the gurney 54. In other embodiments, the support 52 is coupled to and/or part of the gurney 54. The patient 22 is positioned within the room in the extra space behind the gantry 12 (i.e., side 56). As depicted, the patient support 50 is coupled to the table 46. The table 46 and the patient support 50 are disposed on a second side 58 of the gantry 12 (and bore 48) opposite side 56. The structure of the table 46 is as described in FIG. 2. As depicted, the table 46 includes a table base 60 and an upper table 62 coupled to the table base 60. As depicted, the support 52 (e.g., made of plastic, carbon fiber, etc.) is thinner than the patient support 50. As a result, the support 52 is more transmissive (e.g., relative to the patient support 50) to X-rays improving X-ray flux and enabling optimization of X-ray dose during an imaging scan.

During the process of moving the support 52 and the patient 22 into the bore 48, the gantry 12 (and CT system 10) and gurney 54 are kept stationary. The CT system 10 (other than the rotation of the gantry 12 in place) is stationary (e.g., does not move in an axial direction) during the scan. Also, during the scan, a single imaging volume (e.g., utilizing up to 160 mm collimation) may be acquired without moving the patient 22 during the scan (e.g., mid-scan).

Figure 8:
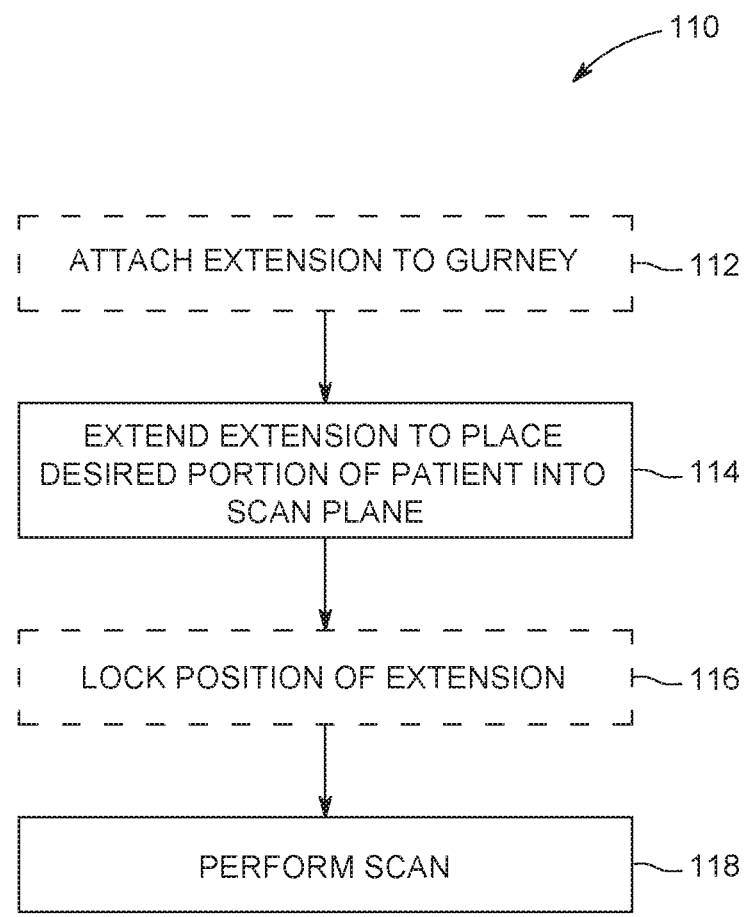
FIG. 8 is a flow chart of an embodiment of a method for positioning a patient for imaging utilizing a support coupled to a mobile patient transport (e.g., gurney).

FIG. 8 is a flow chart of an embodiment of a method 110 for positioning the patient 22 for imaging utilizing the support 52 coupled to the gurney 54. One or more the steps of the method 110 may be carried out utilizing the controllers 28, 30 or other controller. In certain embodiments, the method 100 includes, prior to placing the patient 22 on the gurney, attaching the support 52 (e.g., extension or transfer board) to the gurney 54 (block 112). In certain embodiments, the support 52 may be part of the gurney 54. The method 110 includes extending (e.g., axially) the support 52 (with the patient 22 on it) into the bore 48 to place the portion of the patient 22 to be imaged within the scan plane 72 (block 114). As noted above, during the process of moving the support 52 and the patient 22 into the bore 48, the gantry 12 (and CT system 10) and gurney 54 are kept stationary. With the support 52 and portion of patient 22 to be imaged extending into the bore 48, an entirety of the patient 22 (i.e., patient's weight) is being supported by the support 52 and the gurney 54. Upon getting the patient 22 into position for the scan, in certain embodiments, the method 110 includes subsequently locking a position of the patient support 52 to avoid unintended motion of the patient 22 (block 116). The method 110 further includes performing the scan (e.g., with a stationary CT imaging system 10) to acquire a single imaging volume without moving the patient during the scan (block 118).

Technical effects of the disclosed embodiments include alternative or auxiliary techniques for both preparing a patient for imaging and imaging the patient utilizing a medical imaging system (e.g., computed tomography (CT) or CT/positron emission tomography (PET) imaging system). In particular, a patient (e.g., subject) may be scanned and a single imaging volume (e.g., utilizing 160 millimeter (mm) collimation) acquired without moving the patient during the scan (e.g., mid-scan) while the imaging system is stationary. Instead of the patient being disposed on the patient support (e.g., cradle) coupled to the CT table, another support on the opposite side of the gantry from the CT table and the patient support may be utilized to support at least a majority of the patient during the imaging scan. In certain embodiments, the support may be thinner than the patient support (e.g., cradle) and, thus, more transmissive to X-rays improving X-ray flux and enabling optimization of X-ray dose. In addition, the disclosed embodiments enable an alternative workflow for scans (e.g., for a certain subset of patients) that typically require repositioning of a patient during a scan or do not require a CT table. Further, the handling of the patient (via technologists) is reduced or avoided in positioning them for the scan.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
coupling an extension disposed on a first end of a cradle nearest a gantry bore of a stationary computed tomography (CT) imaging system to a second end of a board nearest the gantry bore, wherein a subject to be imaged is disposed on the board;
positioning the board with the subject on it into the gantry bore via the cradle by pulling on the second end of the board;
partially supporting the subject to be imaged on the board extending from a mobile patient transport into the gantry bore while partially supporting both the subject and the board with the cradle extending from a table; and
acquiring a single imaging volume, during an imaging scan with the stationary CT imaging system, without moving the subject while the subject remains partially supported on the board extending from the mobile patient transport.

2. The method of claim 1, wherein the mobile patient transport and the table are disposed on opposite sides of the gantry bore.

3. The method of claim 1, comprising, subsequent to pulling the board with the subject, locking a position of the cradle relative to the table.

4. The method of claim 1, comprising adjusting a position of the cradle to couple the extension to the second end of the board.

5. The method of claim 1, wherein the second end of the board comprises a corresponding receptacle configured to receive the extension.

6. The method of claim 1, comprising coupling the extension to the cradle.

7. A method, comprising:
coupling an extension disposed on a first end of a cradle nearest a gantry bore of a stationary computed tomography (CT) imaging system to a second end of a board nearest the gantry bore, wherein a subject to be imaged is disposed on the board;
positioning the board both supporting the subject to be imaged and coupled to a mobile patient transport into the gantry bore utilizing the cradle extending from a table by pulling the second end of the board; and
acquiring a single imaging volume, during an imaging scan with the stationary CT imaging system, without moving the subject while the board remains coupled to the mobile patient transport.

8. The method of claim 7, wherein the board partially supports the subject to be imaged on the board extending from the mobile patient transport, and the cradle only partially supports both the subject and the board.

9. The method of claim 7, wherein the mobile patient transport and the table are disposed on opposite sides of the gantry bore.

10. The method of claim 7, comprising adjusting a position of the cradle to couple the extension to the second end of the board.

11. The method of claim 7, wherein the second end of the board comprises a corresponding receptacle configured to receive the extension.

12. The method of claim 7, comprising coupling the extension to the cradle.

13. The method of claim 7, comprising, subsequent to positioning the board with the subject, locking a position of the cradle relative to the table.

* * * * *